United States Patent [19]

Houlihan et al.

[11] Patent Number: 4,914,096

[45] Date of Patent: Apr. 3, 1990

[54] 6-ARYL-SUBSTITUTED-4H-THIENO(2,3-E)(1,2,4)TRIAZOLO(3,4-C)(1,4)DIAZEPINES

[75] Inventors: William J. Houlihan, Mountain Lakes; Seung H. Cheon, Glen Ridge, both of N.J.

[73] Assignee: Sandoz Pharmaceuticals Corp., East Hanover, N.J.

[21] Appl. No.: 331,937

[22] Filed: Mar. 31, 1989

Related U.S. Application Data

[63] Continuation-in-part of Ser. No. 285,579, Dec. 16, 1988, abandoned, which is a continuation of Ser. No. 184,537, Apr. 21, 1988, abandoned.

[51] Int. Cl.⁴ .................... C07D 513/14; A61K 31/55
[52] U.S. Cl. ..................................... 514/220; 540/560
[58] Field of Search ........................ 540/560; 514/220

[56] References Cited

U.S. PATENT DOCUMENTS 4,201,712  5/1980  Weber et al. .................... 540/560

Primary Examiner—Robert T. Bond
Attorney, Agent, or Firm—Gerald D. Sharkin; Robert S. Honor; Joseph J. Borovian

[57] ABSTRACT

The invention discloses certain 6-aryl-substituted-4H-thieno[2,3-e][1,2,4]triazolo[3,4-c][1,4]diazepines useful as PAF inhibitors, pharmaceutical compositions containing said compounds as an active ingredient thereof and a method of using such compositions for inhibiting PAF-induced blood platelet aggregation, PAF-mediated bronchoconstriction and extravasation, PAF-induced hypotension, PAF-induced ischemic bowel disease and PAF-mediated, endotoxin induced lung injury, for controlling hyperreactive airways and for protecting against endotoxin-induced hypotension and death.

23 Claims, No Drawings

6-ARYL-SUBSTITUTED-4H-THIENO(2,3-E)(1,2,4)TRIAZOLO(3,4-C)(1,4)DIAZEPINES

This is a continuation-in-part of U.S. patent application Ser. No. 07/285,579, filed Dec. 16, 1988, now abandoned, which in turn is a continuation of U.S. patent application Ser. No. 07/184,537, filed Apr. 21, 1988, now abandoned.

The present invention relates to certain 6-aryl-substituted-4H-thieno[2,3-e][1,2,4]triazolo[3,4-c][1,4]diazepines and to their use as platelet activating factor (PAF) receptor antagonists and as inhibitors of PAF-induced blood platelet aggregation. The invention also relates to pharmaceutical compositions containing the afore-mentioned compounds as an active ingredient thereof and to the method of using such compositions for inhibiting PAF-mediated bronchoconstriction and extravasation, PAF induced hypotension, PAF-involved ischemic bowel disease and PAF-mediated, endotoxin-induced lung injury, for hyperreactive airways control induced by PAF or allergen, and for protection against endotoxin-induced hypotension and death.

Blood platelets, also called thrombocytes, are well recognized as important cellular elements that circulate in the blood. Their role is to staunch bleeding by forming clots in broken blood vessels, i.e., they are nature's corks. They have, however, been implicated in a variety of immunologically mediated forms of tissue injury. Their participation in these processes involves the release of platelet activating factor (PAF) which in turn interacts with the platelets, inducing aggregation and secretion of granular constituents. As a further consequence of platelet activation, there may result a fatal reaction consisting of acute pulmonary hypertension, right heart dilation, systemic hypotension, significant increases in pulmonary vascular resistance, a decrease in dynamic lung compliance and often complete pulmonary apnea. More recently, evidence has been obtained which appears to implicate platelet activating factor in the formation of fibromuscular lesions of the arterial walls of the aorta and coronary arteries, thereby contributing to the development of atherosclerosis. Further, the possible role of PAF in ischemic bowel disease, particularly necrotizing enterocolitis (NEC) has recently been described, thereby implicating PAF in the development of disorders leading to bowel necrosis. Still further, evidence has been obtained which supports the hypothesis that PAF is an important mediator of endotoxin-induced lung injury, -pulmonary hypertension, -hypoxemia and -reduced cardiac output.

The existence of platelet activating factor was proposed in an article by Henson, P. M., Journal of Experimental Medicine 131, 287 (1970). However, due to the limited quantities of material available for study, great difficulty was encountered in defining the chemical structure and biochemical activity of PAF.

One of the earlier reports on the chemical nature of PAF was that of Benveniste, J., Nature 249, 581 (1974), wherein the physiochemical characteristics of PAF were reported. A later study of Benveniste, J. et al., Nature 269, 170 (1977) reported on the purification of PAF isolated by successive thin layer chromatography. A more recent study by Hanahan, et al. in the J. of Biol. Chem. 225: 5514–5516 (June 1980) confirmed that the compounds, 1-O-alkyl-2-acetyl-sn-glyceryl-3-phosphoryl-choline (AGEPC), and PAF are one and the same composition. Since that time, many research endeavors have been directed to the synthesis of compounds structurally related to that of PAF in an effort to uncover compounds useful in the inhibition of platelet activating factor.

The essence of the present invention is the discovery that certain thienotriazolodiazepine compounds of formula I:

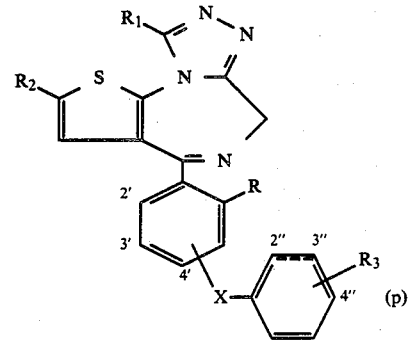

where
R is hydrogen or chloro;
$R_1$ is hydrogen; methyl or cyclopropyl;
$R_2$ is hydrogen; methyl; ethyl; a group of the formula

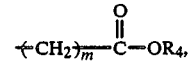

where m is 1 to 4 and $R_4$ is methyl, ethyl or an alkali metal cation; a group of the formula

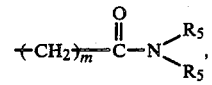

where m is as defined above and each $R_5$, independently, is straight or branched chain $C_{1-3}$alkyl, or the two $R_5$'s together with the nitrogen atom to which they are attached form a group of the formula

where n is 4 or 5, or a group of the formula

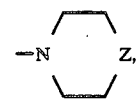

where Z is —O—, —S— or —NCH$_3$—; or a group of the formula

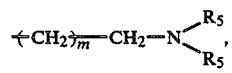

where m and the $R_5$'s are as defined above;
X is $-(CH_2)_m$, where m is as defined above; —OCH$_2$— or —CH$_2$OCH$_2$—;

p is 0 or an integer 1 to 3; and $R_3$ is chloro; fluoro; methyl; t-butyl; $OR_6$, where $R_6$ is methyl or ethyl; or a group

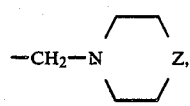

where Z is as defined above, with the provisos that: (1) when R is hydrogen, X is only in the 3'- or 4'-positions, and when R is chloro, X is only in the 4'-position; (2) when $R_3$ is chloro, fluoro or methyl, the maximum number of said substituents is two; (3) when $R_3$ is t-butyl or a group

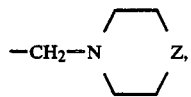

then p is 1; and (4) when p is 2, the $R_3$'s cannot be in the 2''- and 6''-positions, simultaneously;

and their pharmaceutically acceptable acid addition salts, where such may exist, are useful as PAF-receptor antagonists and as inhibitors of PAF-induced blood platelet aggregation.

Of the compounds of formula I, preferred are the compounds of formula I':

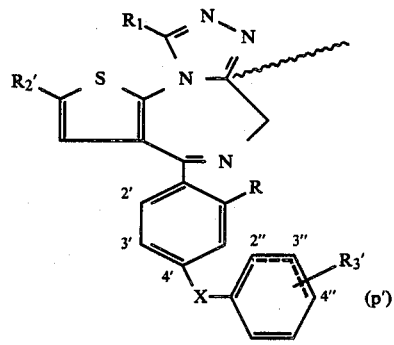

I' where $R_2'$ is hydrogen; a group of the formula

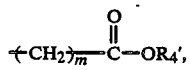

where $R_4'$ is methyl, sodium, potassium and m is as defined above; or a group of the formula

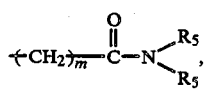

where m and the $R_5$'s are as defined above; p' is an integer 1 to 3;

$R_3'$ is $OR_6$, where $R_6$ is as defined above; or a group

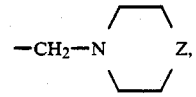

where Z is as defined above; and

R, $R_1$ and X are as defined above; with the provisos that: (1) when $R_3'$ is a group

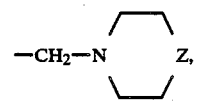

then p' is 1; and (2) when p' is 2, the $R_3''$'s cannot be in the 2''- and 6''-positions, simultaneously;

and their pharmaceutically acceptable acid addition salts, where such may exist.

The more preferred compounds of formula I are the compounds of formula I'':

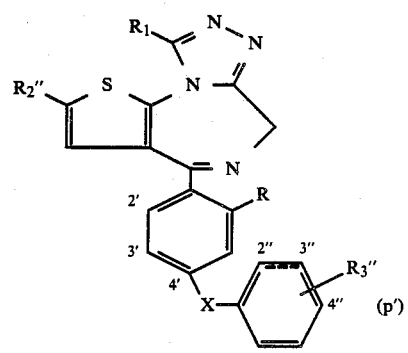

I'' where $R_2''$ is hydrogen; a group of the formula

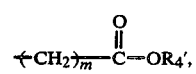

where m and $R_4'$ are as defined above; or a group of the formula

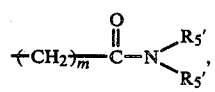

where m is as defined above and the $R_5''$'s together with the nitrogen atom to which they are attached form a group of the formula

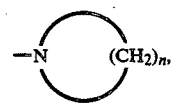

where n is as defined above, or a group of the formula

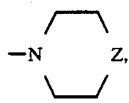

where Z is as defined above;

R₃″ is OR₆, where R₆ is as defined above; and

R, R₁, X and p′ are as defined above, with the proviso that when p′ is 2, the R₃‴s cannot be in the 2″- and 6″-positions, simultaneously;

and their pharmaceutically acceptable acid addition salts, where such may exist.

The even more preferred compounds of formula I are the compounds of formula I‴:

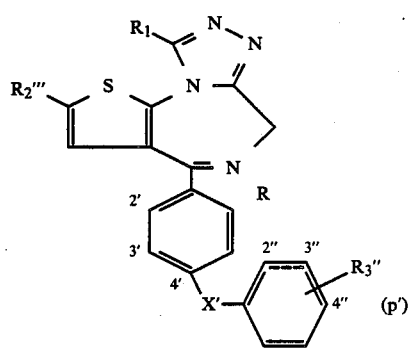

where $R_2'''$ is hydrogen; a group of the formula

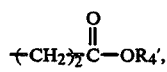

where $R_4'$ is as defined above; or a group of the formula

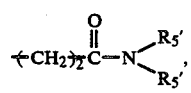

where the $R_5'$s are as defined above;

X′ is $+CH_2+_m$, where m is as defined above; and

R, R₁, p′ and R₃″ are as defined above, with the proviso that when p′ is 2, the R₃‴s cannot be in the 2″- and 6″-positions, simultaneously;

and their pharmaceutically acceptable acid addition salts, where such may exist.

The still even more preferred compounds of formula I are the compounds of formula $I^{IV}$:

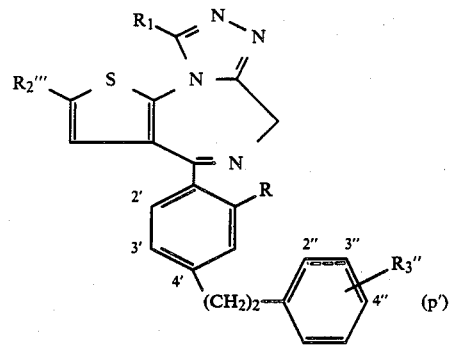

where

R, R₁, R₂‴, p′ and R₃″ are as defined above, with the proviso that when p′ is 2, the R₃‴s cannot be in the 2″- and 6″-positions, simultaneously;

and their pharmaceutically acceptable acid addition salts, where such may exist.

The compounds of formula I where R₂ is hydrogen and R, R₁, X, p and R₃ are as defined above may be prepared by a seven-step reaction as set forth below:

STEP 1

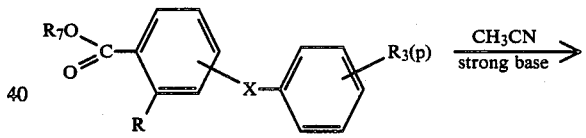

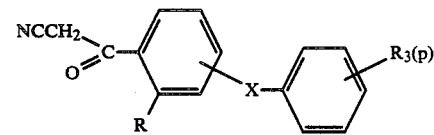

where R₄ is methyl or ethyl, and R, X, p and R₃ are as defined above.

STEP 2

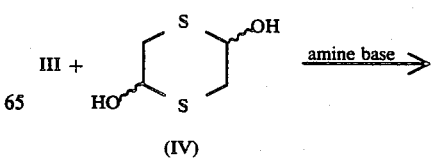

-continued

STEP 2

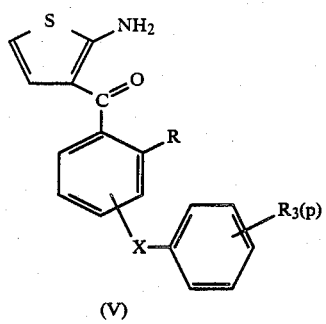

(V)

where R, X, p and R₃ are as defined above.

STEP 3

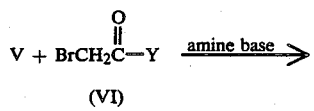

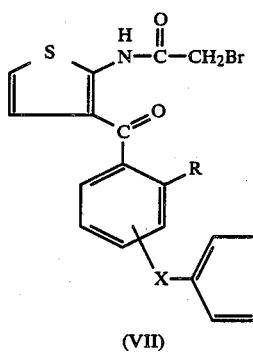

(VII)

where Y is chloro or bromo and R, X, p and R₃ are as defined above.

STEP 4

VII $\xrightarrow{NH_3}$

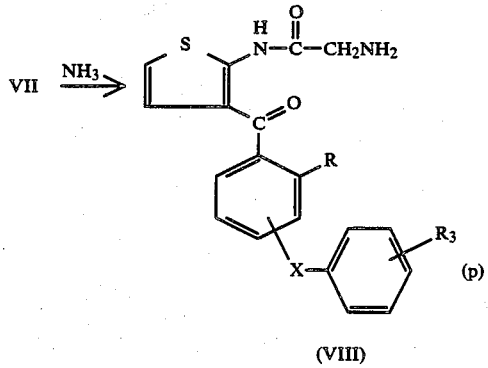

(VIII)

where R, X, p and R₃ are as defined above.

STEP 5

VIII $\xrightarrow{SiO_2 \text{ (activated)}}$

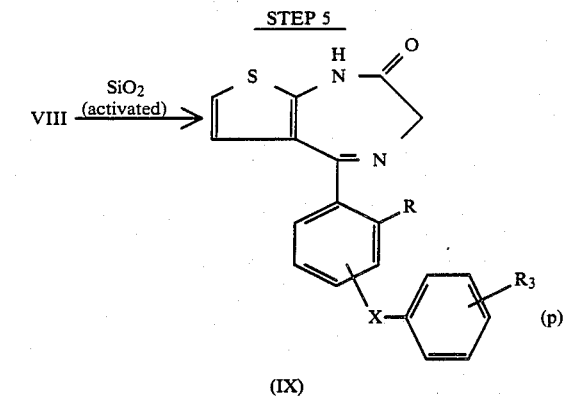

(IX)

where R, X, p and R₃ are as defined above.

STEP 6

XI $\xrightarrow{\text{sulfur source}}$

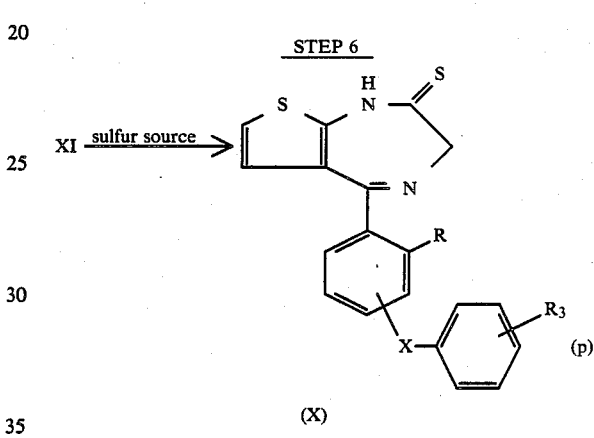

(X)

where R, X, p and R₃ are as defined above.

Step 7

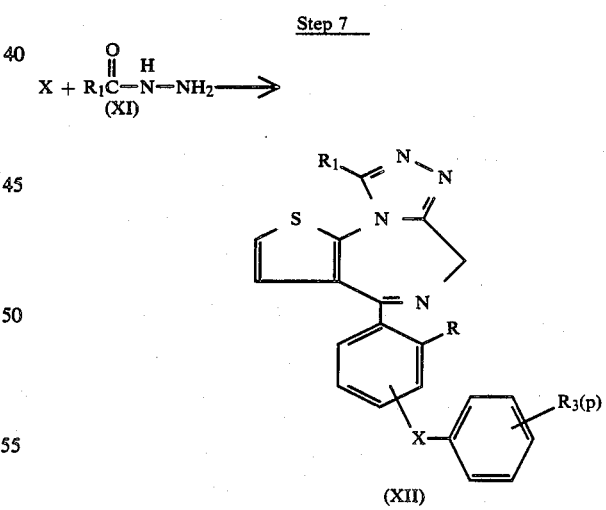

(XII)

where R, R₁, X, p and R₃ are as defined above.

With respect to the individual steps, Step 1 involves the reaction of a benzoate compound of formula II with acetonitrile in the presence of a strong base, e.g., an alkali metal hydride such as sodium hydride or an alkali metal alkoxide such as potassium methoxide or ethoxide, to yield a nitrile compound of formula III. The reaction is typically carried out in an inert, organic solvent, e.g. a di-lower alkyl ether such as methyl t-butyl ether or a cyclic ether such as tetrahydrofuran, a polar, aprotic solvent such as dimethylformamide, or a mixture of a cyclic ether and a polar, aprotic solvent, e.g., a mixture of tetrahydrofuran and dimethylformamide. As to reaction conditions, the reaction is typically carried out at a temperature of from 30° to 75° C. for a period of between 1 and 4 hours.

Step 2 involves the reaction of a nitrile compound produced in Step 1, i.e., a compound of formula III, with the compound of formula IV, i.e., 1,4-dithiane-2,5-diol, in the presence of an amine base such as triethylamine or N-methylpyrrolidine to yield a thienylphenylmethanone compound of formula V. The reaction is generally carried out in a polar, aprotic solvent such as dimethylformamide or dimethylacetamide at a temperature of from 25° to 75° C. for a period of between 2 and 8 hours.

As to Step 3, it involves the reaction of a thienylphenylmethanone compound produced in Step 2, i.e., a compound of formula V, with a compound of formula VI, i.e., bromoacetyl bromide or chloride, in the presence of an amine base such as pyridine, triethylamine, N,N-diisopropylethylamine or N-methylpyrrolidine to yield a thienyl acetamide compound of formula VII. The reaction is usually carried out in an inert, organic solvent, e.g., an aromatic hydrocarbon such as toluene or benzene, a halogenated, aliphatic hydrocarbin such as methylene chloride or chloroform, or a cyclic ether such as tetrahydrofuran. As to reaction conditions, the reaction is generally carried out at a temperature of from 0° to 35° C. for a period of between 12 hours and 3 days.

In Step 4, a thienyl acetamide compound produced in Step 3, i.e., a compound of formula VII, is treated with ammonia gas to yield a compound of formula VIII. The reaction is typically conducted in an inert, organic solvent, e.g., a di-lower alkyl ether such as methyl t-butyl ether, a lower alkanol such as methanol, a cyclic ether such as tetrahydrofuran, or a mixture of a lower alkanol and a cyclic ether, e.g., a mixture of methanol and tetrahydrofuran. As regards reaction conditions, the reaction is normally conducted at a temperature of from 0° to 35° C. for a period of between 12 and 36 hours.

Step 5 involves treating a compound produced in Step 4, i.e., a compound of formula VIII, with activated silica to yield a diazepin-2-one compound of formula IX. The reaction is typically conducted in an inert, organic solvent, e.g., an aromatic hydrocarbon such as toluene, benzene or xylene, or a cyclic hydrocarbon such as cyclohexane, at a temperature of from 60° to 150° C. for a period of between 1 and 5 hours.

Step 6 involves the conversion of a diazepin-2-one compound produced in Step 5, i.e., a compound of formula IX, to a diazepin-2-thione compound of formula X by subjecting a compound of formula IX to a sulfur source, e.g., phosphorus pentasulfide or Lawesson's Reagent (2,4-bis[4-,methoxyphenyl]-1,3-dithia-2,4-diphosphetane-2,4-disulfide). The conversion is usually carried out in a solvent such as pyridine, N-methylpyridine or quinoline, or in an aromatic hydrocarbon such as benzene or toluene at a temperature of from 80° to 120° C. for a period of between 30 minutes and 4 hours.

The last step, viz., Step 7, is concerned with the reaction of a diazepin-2-thione compound produced in Step 6, i.e., a compound of formula X, with a hydrazide compound of formula XI to yield a triazolodiazepine compound of formula XII. The reaction is typically carried out in an inert, organic solvent, e.g., an aromatic hydrocarbon such as benzene or toluene, or preferably in diglyme or another lower alkoxyethyl ether. As to reaction conditions, the reaction is conducted at a temperature of from 90° to 130° C. for a period of between 2 and 10 hours.

The compounds of formula I where $R_2$ is methyl, ethyl, a group of the formula

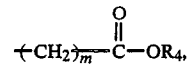

where $R_4$ is methyl or ethyl and m is as defined above, or a group of the formula

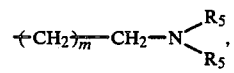

where m and the $R_5$'s are as defined above, and $R_1$, X, p and $R_3$ are as defined above may be prepared by the following reaction scheme:

REACTION A

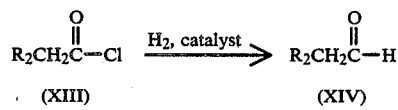

where $R_2$ is methyl, ethyl, a group of the formula

or a group of the formula

REACTION B

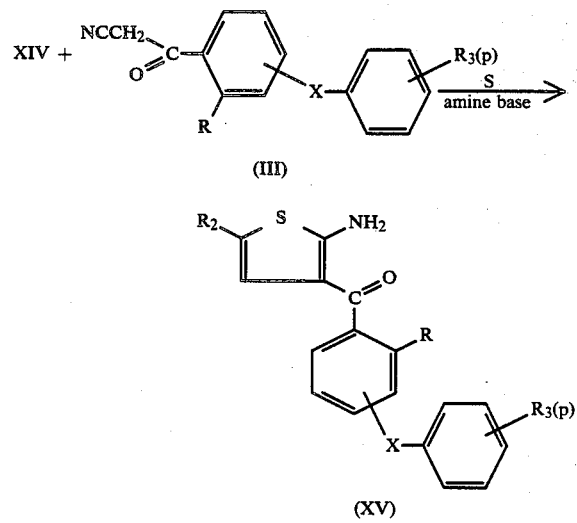

where $R_2$ is as set forth in Reaction A, and R, X, p and $R_3$ are as defined above.

REACTION C

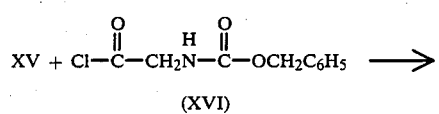

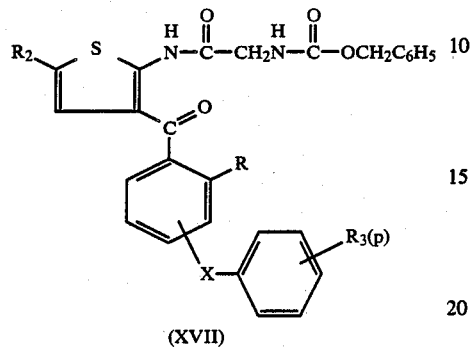

where $R_2$ is as set forth in Reaction A, and R, X, p and $R_3$ are as defined above.

REACTION D

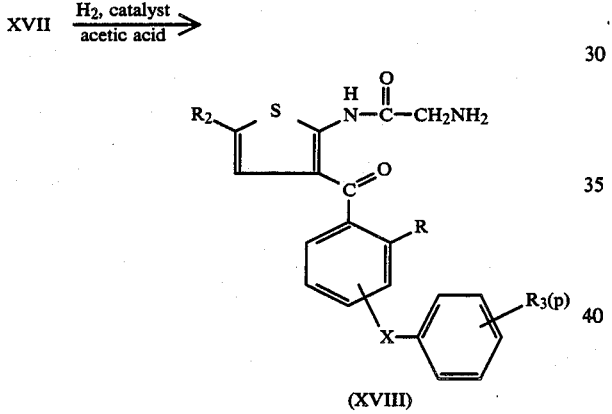

where $R_2$ is as set forth in Reaction A, and R, X, p and $R_3$ are as defined above.

REACTION E

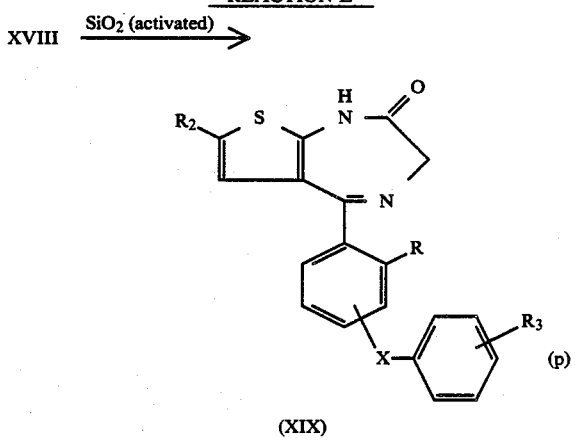

where $R_2$ is as set forth in Reaction A, and R, X, p and $R_3$ are as defined above.

REACTION F

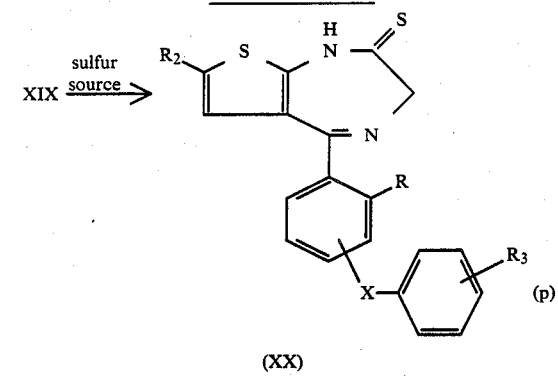

where $R_2$ is as set forth in Reaction A, and R, X, p and $R_3$ are as defined above.

REACTION G

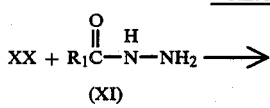

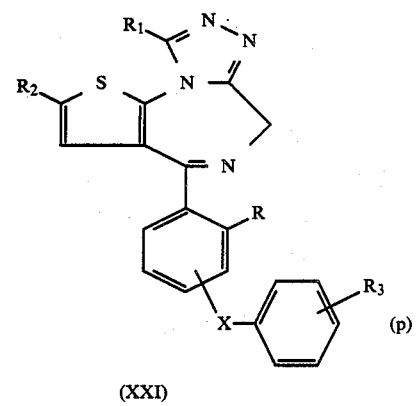

where $R_2$ is as set forth in Reaction A, and R, $R_1$, X, p and $R_3$ are as defined above.

As to the reactions individually, Reaction A involves the catalytic reduction of an acid chloride compound of formula XIII (Rosenmund's Reaction) to an aldehyde compound of formula XIV. The reaction is typically carried out by dissolving the acid chloride compound in an inert, organic solvent, e.g., a cyclic ether such as tetrahydrofuran or dioxane, adding a catalyst such as palladium or platinum or carbon and a mono- or di-lower alkyl pyridine, e.g., 2,6-lutidine (as a poison for the catalyst), and subjecting the resultant mixture to a pressure of between 30 and 60 lbs. of hydrogen gas at a temperature of from 15° to 25° C. for a period of between 2 and 6 hours.

Reaction B involves the reaction of an aldehyde compound produced by Reaction A, i.e., a compound of formula XIV, with a nitrile compound of formula III and sulfur to yield a compound of formula XV. The reaction is typically carried out in a polar, aprotic solvent such as dimethylformamide and in the presence of an amine base such as triethylamine or N-methylpyrrolidine. As to reaction conditions, the reaction is typically carried out at a temperature of from 50° to 100° C. for a period of between 1 and 4 hours.

Reaction C is directed to the reaction of a compound produced in Reaction B, i.e., a compound of formula XV, with a compound of formula XVI (prepared by the addition of phosphorus pentachloride to a suspension of carbobenzyloxyglycin in dry ether and stirring the resultant mixture at ambient temperatures for between 30 and 90 minutes) to yield a compound of formula XVII. The reaction is typically carried out in an inert, organic solvent, e.g., a halogenated, aliphatic hydrocarbon such as methylene chloride or chloroform, at a temperature of from 10° to 30° C. for a period of between 8 and 20 hours.

Reaction D involves the hydrogenolysis of a compound produced in Reaction C, i.e., a compound of formula XVII, by dissolving said compound in glacial acetic acid, adding either palladium or platinum on carbon, and subjecting the resultant mixture to a pressure of between 10 and 30 lbs. of hydrogen gas at a temperature of from 15° to 25° C. for a period of between 10 and 20 hours to yield a compound of formula XVIII.

In Reaction E, a compound produced in Reaction D, i.e., a compound of formula XVIII, is treated with activated silica to yield a diazepine compound of formula XIX. As to reaction conditions, they are analogous to those set forth above in Step 5.

Reaction F involves the conversion of a diazepine compound produced in Reaction E, i.e., a compound of formula XIX, to a thieno diazepine compound of formula XX by subjecting a compound of formula XIX to a sulfur source, e.g., phosphorus pentasulfide or Lawesson's Reagent (2,4-bis[4-methoxyphenyl]-1,3-dithia-2,4-diphosphetane-2,4-disulfide). The conversion is carried out under the analogous conditions set forth above in Step 6.

The last reaction, viz., Reaction G, is concerned with the reaction of a thienodiazepine compound produced in Reaction F, i.e., a compound of formula XX, with a hydrazide compound of formula XI to yield a triazolodiazepine compound of formula XXI. As to reaction conditions, they are identical to that set forth above in Step 7.

The compounds of formula I where $R_2$ is a group of the formula

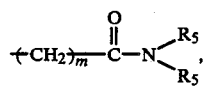

where m and the $R_5$'s are as defined above, and $R_1$, X, p and $R_3$ are as defined above may be prepared by the following reaction employing a compound of formula XXI where $R_2$ is a group of the formula

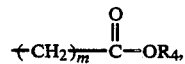

where m and $R_4$ are as defined above, as the starting material:

REACTION H

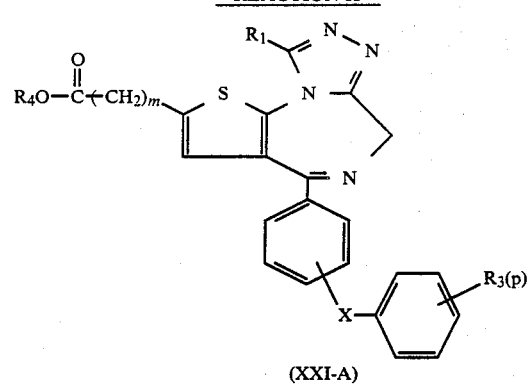

(XXI-A)

+

(XXII)

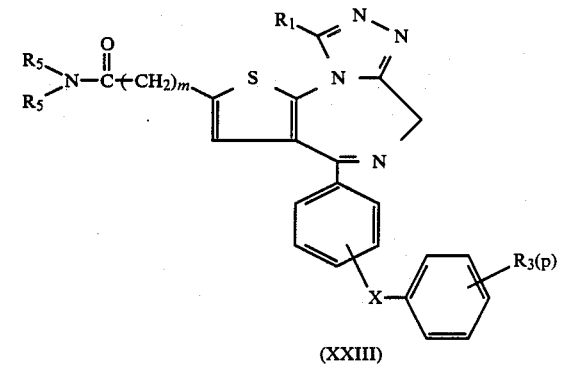

(XXIII)

where $R_1$, X, p, $R_3$, m, $R_4$ and the $R_5$'s are defined above.

In the above reaction, a particular triazolo diazepine compound produced in Reaction G, i.e., an ester compound of formula XXI-A, is reacted with a secondary amine compound of formula XXII to yield a compound of formula XXIII. The reaction is generally carried out at a temperature of from 150° to 190° C. for a period of between 4 and 8 hours.

The compounds of formula I where $R_2$ is a group of the formula

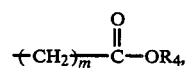

where $R_4$ is an alkali metal cation and m is as defined above, and $R_1$, X, p and $R_3$ are as defined above may be prepared by the following reaction employing a compound of formula XXI where $R_2$ is a group of the formula

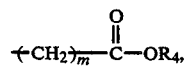

where $R_4$ is methyl or ethyl and m is as defined above, as the starting material:

REACTION I

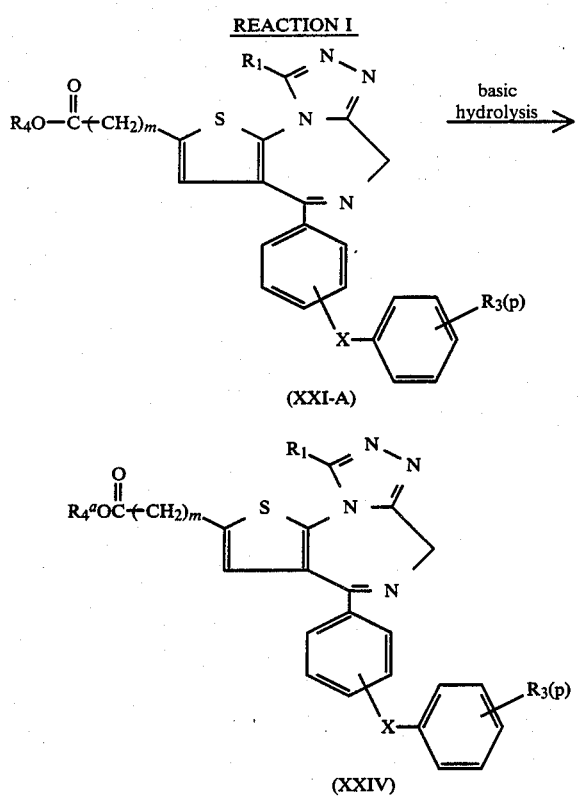

where R₄ is methyl or ethyl, R₄ᵃ is an alkali metal cation and $R_1$, X, p, $R_3$ and m are as defined above.

In the above reaction, a particular triazolo diazepine compound produced in Reaction G, i.e., an ester compound of formula XXI-A, is subjected to basic hydrolysis, e.g., an aqueous solution of an alkali metal hydroxide, preferbly sodium or potassium hydroxide. The hydrolysis is optionally conducted in the presence of an inert, organic solvent, e.g., a lower alkanol such as methanol or ethanol, at a temperature of from −10° C. to 30° C. for a period of from 15 minutes to about 3 hours to yield a compound of formula XXIV.

The compounds of formula II, IV, VI, XI, XIII, XVI and XXII are either known and obtained by methods described in the literature, or where not known, may be obtained by methods analogous to those described in the literature.

The product of each reaction may, if desired, be purified by conventional techniques such as recrystallization (if a solid), column chromatography, preparative thin layer chromatography, gas chromatography (if sufficiently volatile) or fractional distillation under high vacuum (if sufficiently volatile). Often, however, the crude product of one reaction may be employed in the following reaction without purification.

As previously indicated, pharmaceutically acceptable acid addition salts (i.e., those salts which do not significantly increase the toxicity of the base compound) of the compounds of formula I, where such may exist, are included within the scope of this invention. These include salts of mineral acids such as hydrochloric, hydrobromic, phosphoric and sulfuric acids, as well as salts of organic acids such as tartaric, acetic, citric, malic, maleic, methanesulfonic and gluconic acids.

All of the compounds of formula I, as well as their pharmaceutically acceptable acid addition salts, are useful as platelet activating factor inhibitors as indicated by their ability to inhibit platelet activating factor (PAF)-induced human platelet aggregation in vitro according to the Platelet Aggregation Inhibition Assay test (PAIA test) as follows:

Human subjects are kept aspirin free for one week and fasted overnight. Platelet rich plasma (PRP) is prepared by centrifugation (200×g.) of freshly drawn blood, anti-coagulated within 0.38% sodium citrate (final concentration). Platelet count is adjusted to 250,000 per µl using platelet poor plasma (PPP) obtained by a second centrifugation (700×g.) of the blood sample. An aliquot (0.38 ml) of the PRP is dispensed into cuvettes and maintained at room temperature (22° C.) until used (but for not more than two hours). The PRP-containing cuvettes are incubated at at 37° C. and stirred at 900 rpm within a Payton Aggregometer which is activated to follow the light deflection pattern prior to the addition of the test compound. The test compound (dissolved in a suitable solvent mixture which does not influence platelet aggregation) is then added to a PRP-containing cuvette in an amount sufficient to provide a final concentration of 100 µM. Between one and two minutes after the addition of the test compound, the aggregation inducing agent (C-16 PAF-Sandoz-Hanover), dissolved in a buffer consisting of 0.01M Tris-Tyrodes buffer with 0.25% bovine serum albumin (pH 7.4), is added to the PRP-containing cuvettes in an amount predetermined to give a consistent aggregation response (either 0.1 µM or 0.01 µM). All aggregations are allowed to proceed for 6 minutes from the addition of the inducing agent. The aggregation response is quantitated by determining the area under the curve (AUC). The AUC calculated for the inducing agent alone is considered to be one hundred percent. The potential percent inhibition of the aggregation response is determined by dividing the AUC generated in the presence of the compound by the AUC of the inducing agent alone, multiplying by 100 and then subtracting from 100. The compounds demonstrating greater than 50% inhibition at 100 µM are evaluated at lower concentrations to generate an IC₅₀ (50% inhibitory concentration) value.

Moreover, it has been found that all of the compounds of formula I are useful as platelet activating factor receptor antagonists as indicated by their ability to inhibit specific binding of (³H)-PAF to platelets according to the Human Platelet PAF Receptor Assay test (Test A) as follows:

Human blood is obtained by venipuncture of healthy, human donors into an anti-coagulant mixture containing 3.15% of trisodium citrate and 20 µg/ml of Prostaglandin I₂ (PGI₂) in a ratio of blood to anti-coagulant of 9:1. Platelet rich plama (PRP) is prepared by centrifugation (250×g) of the blood for 20 minutes at room temperature. The PRP is then centrifuged (900×g) for 10 minutes at room temperature and the platelet pellet is washed two times with Tris-Tyrode's (TT) solution having a pH of 7.4 and containing 0.25% bovine serum albumin (BSA), and to which has been added PGI₂ at a final concentration of 0.3 g/ml. The platelets are resuspended at 350,000 µl in TT/BSA containing 1.4 mM CaCl₂.2H₂O and 0.7 mM MgCl₂.6H₂O. All of the tests are conducted in duplicate and each of the test compounds is evaluated at concentrations of 100, 50, 1 and 0.1 µM. For each determination, the following solutions are mixed:

500 μl of the above-described platelets;

10 μl of ($^3$H)-PAF (40,000 counts per minute (cpm) to a final concentration of 1.5 μM); and either 10 μl of the test compound at 50× the desired final concentration, 10 μl of vehicle (total bound), or (10 μl of 1.85×10$^{-5}$M cold PAF (non-specifically bound).

Each mixture is allowed to incubate at room temperature for one hour, after which time the reaction is terminated by the addition of 500 μl of ice cold TT/BSA and centrifugation (900×g) at 4° C. for 10 minutes. The resultant supernatant is aspirated into scintillation vials and the pellet is washed with 250 mL. of ice cold TT/BSA and centrifuged (900×g) at 4° C. for 10 minutes. The supernatants are then aspirated into the same scintillation vials as before and 10 ml. of Scintiverse II (a liquid scintillation cocktail) is added to and mixed therewith. The pellets are resuspended in 500 μl of Scintiverse II and mixed well. An additional 2 ml. of Scintiverse II is then added to the vials and, after mixing, the vials are counted for 1 minute in a liquid scintillation spectrometer. The amount of specific binding is calculated as the difference in cpm between the total bound ($^3$H)-PAF and non-specifically bound ($^3$H)-PAF. The percent inhibition of specific binding is determined by dividing the cpm specifically bound in the presence of the test compound by the cpm specifically bound in total, multiplying by 100 and then subtracting from 100. An IC$_{50}$ (50% inhibitory concentration) value is generated by evaluating the test compound over the full concentration range.

Furthermore, in view of their usefulness as PAF receptor antagonists, the compounds of formula I have been found useful as inhibitors of PAF-mediated bronchoconstriction, which property was evaluated by the PAF-induced Pulmonary Inflation Pressure (PIP) Increase test (Test B) as follows:

Male guinea pigs, weighing between 300 and 400 gm, are anesthetized, after which time trachea tube, carotid and jugular catheters are inserted. The test animal is then force ventilated employing a small animal Harvard respirator and the resistance to lung inflation (PIP) is measured utilizing a pressure transducer and recorder. The test compound is administered orally at 30 minutes prior to, intravenously (jugular) at 5 minutes prior to, or intraarterially at 1 to 5 minutes prior to the introduction of PAF. The PAF (C$_{18}$-Sandoz, Hanover) is dissolved in Tris-Tyrode's bovine serum albumin buffer and administered intravenously (jugular) at 100 ng/kg. Any blood pressure measurements taken are recorded from a transducer attached to the carotid catheter. Two responses are noted in the PIP recordings after the PAF is administered: (1) an immediate response which, in PAF-only treated test animals, averages out to between 70% and 80% more than the baseline PIP values. (This early response is also the greatest response and is, therefore, termed maximal PIP); and (2) the long term (at least 30 minutes) PIP response which slowly decreases to baseline. A reading at 15 minutes after the administration of PAF is termed the endpoint PIP. The effect of the test compound on the PIP response is determined by the difference between the percent increase in maximal PIP over baseline for the test animal to which has been administered PAF and the test compound compared to the test animal to which only PAF has been administered to generate an ED 5 C (dose needed to effect a 50% response).

Still further, the compounds of formula I are useful as inhibitors of PAF-mediated extravasation (the extrusion of plasma from the lumen of the blood vessels into the vessel wall and surrounding tissues) measured as a function of hemoconcentration according to the PAF-induced Extravasation test (Test C) as follows:

Male guinea pigs, weighing between 300 and 400 gm, are anesthetized, after which time a femoral catheter is inserted. The test compound is administered intraarterially at one to five minutes prior to the introduction of PAF. The PAF (C$_{18}$-Sandoz, Hanover) is dissolved in Tris-Tyrode's bovine serum albumin buffer and administered intravenously (jugular) at 100 ng/kg.

To determine the hematocrit value, which is employed to index hemoconcentration and is defined as the percent of packed red blood cells in a sample of blood which is centrifuged to separate plasma from the cellular components, blood samples are collected in 50 μl heparinized hematocrit tubes. These samples are taken just prior to the injection of PAF, one minute subsequent to the injection of PAF and every two minutes thereafter until 15 minutes has lapsed subsequent to the injection of PAF. The tubes are then centrifuged and the percent of packed red blood cells (hematocrit) is measured (PAF induces a maximal increase in hematocrit at 5 to 7 minutes subsequent to the injection of PAF). The percent increase in hematocrit over the value prior to the injection of PAF is calculated. The hematocrit values obtained with the test compound are compared to the hemoconcentration values obtained with PAF alone and are expressed as percent inhibition of percent increase in hematocrit. From the values obtained, an ED$_{50}$ is generated.

Yet still further, the compounds of formula I are useful as inhibitors of PAF-induced hypotension as measured by their ability to inhibit the lowering of blood pressure levels induced by PAF according to the following test (Test D):

Male Wistar rats, weighing approximately 300 gm, are anesthetized and their carotid arteries cannulated to enable their diastolic and systolic arterial blood pressure measurements to be recorded. PAF is then administered intravenously at either 100 or 500 ng/kg, and the blood pressure drop (within 10 sec.) and recovery time required to reach the pre-injection blood pressure level are measured. At 100 ng/kg, a 30% decrease in blood pressure and a 3 to 4 minute recovery time are observed, whereas at 500 ng/kg, a 52% decrease in blood pressure and a 10 minute recovery time are observed. In order to measure the effectiveness of a compound for both the inhibition of blood pressure decreases and shortening of the recovery time, the test compound is administered intravenously over a range of between 5 and 7 dosage levels (1 or 2 test animals per dose) and between 1 and 5 minutes prior to the introduction of PAF to generate an ED$_{50}$.

Yet even still further, the compounds of formula I are useful as inhibitors of PAF-induced ischemic intestinal necrosis, which property can be measured in accordance with the following test (Test E):

Following essentially the procedure of F. Gonzalez-Crussi and W. Hsueh published in J. Amer. Pathol., 112, pgs. 127–135 (1983), male Sprague-Dawley rats, weighing approximately between 260 and 300 g, are anesthetized and their carotid arteries cannulated and connected to a blood pressure transducer and recorder. The test compound is introduced into a cannula inserted into the jugular vein at a time 10 minutes prior to the administration of PAF. The abdomen is then incised along the midline and 2 μg of PAF or 20 μg of LPS (lipopolysaccharide) immediately followed by 1 μg of PAF are injected into the abdominal aorta at the level of the renal artery. The abdominal incision is then covered with saline-moistened gauze and the intestine exposed and examined periodically up to 2 to 3 hours prior to sacrifice. Into the jugular vein is then injected 5 ml of 2% Evans Blue to assess the degree of intestinal perfusion. Blocks of intestinal tissue are then taken for microscopic examination to determine either the extent of necrosis or to verify the absence of necrosis when inhibited by the test compound. Microscopic changes in the intestine are assessed by hematoxylin and eosin staining. The test compound is assessed for its ability to alleviate or present the development of gross and microscopic lesions and may be expressed in terms of the number of animals in which inhibition is observed relative to the control (taken to be 100%).

Yet even still further more, the compounds of formula I are useful as inhibitors of PAF-mediated, endotoxin-induced lung injury and, analogously, endotoxin-induced-septic shock and adult respiratory distress syndrome. The ability of the compounds of formula I to inhibit PAF-mediated, endotoxin-induced lung injury can be measured in accordance with the test presented by S. Chang at the 2nd International Conference on *Platelet Activating Factor and Structurally Related Alkyl Ether Lipids* in Gatlinburg, Tenn. on Oct. 26–29, 1986 (Test F).

Based on previous reports that lung tissue and blood PAF increased in endotoxin-treated rats, it was determined that the intraperitoneal administration of 2 mg/kg of endotoxin (*S. enteritidis*) causes acute lung injury, as assessed by the extravascular accumulation of water and $^{125}$I-albumin in perfused lungs isolated from rats ninety minutes following in vivo endotoxin treatment. Thus, the wet lung/body weight ratio (as an index of lung water content) increases from 5.35±0.48 to 8.26±0.36 and the albumin leak index increases from 0.46±0.09 to 1.01±0.07.

In order to measure the effectiveness of a compound as an inhibitor of endotoxin-induced lung injury, the test compound is administered intraperitoneally prior to the in vivo endotoxin treatment.

The ability of the compounds of formula I to inhibit PAF-mediated, endotoxin-induced septic shock can be measured in accordance with the test presented by C. N. Sessler, et al at the Annual Meeting of the American Federation for Clinical Research in New Orleans, La. during January, 1987.

All sheep are prepared for testing employing the Chronic Sheep Lung Lymph preparation which is well documented in the literature, with the modifications that chronic tracheostomies are performed on the test animals and pleural pressure catheters inserted at the time of the initial surgery. All catheters are brought to the outside through stab wounds in the skin, the chest is closed and the test animals are allowed to recover for several days until they appear healthy and lung lymphs are free of blood before experiments are commenced.

In order to measure the effectiveness of a compound as an inhibitor of some of the important hemodynamic effects of endotoxin on septic shock, 1.3 ug/kg of endotoxin or saline is administered to groups of test animals intravenously over a 30 minute period and 20 mg/kg of the test compound or saline is administered intravenously over a five-hour period. The pulmonary arterial pressure (PAP), cardiac output (CO) and partial oxygen pressure (PO$_2$) are monitored continuously over the five-hour period.

The ability of the compounds of formula I to inhibit PAF-mediated, endotoxin-induced adult respiratory distress syndrome can be measured in accordance with the test presented by B. W. Christman, et al at the Annual Meeting of the American Thoracic Society and American Lung Association on May 10th–13th 1987.

In order to measure the effectiveness of a compound as an inhibitor of some of the important hemodynamic effects of endotoxin on adult respiratory distress syndrome, 0.5 ug/kg of *E. coli* endotoxin over a 20 minute period, 20 mg/kg/hr of the test compound for 6 hours, or 0.5 ug/kg of *E. coli* endotoxin 1 hour after commencing 20/kg/hr of the test compound for 6 hours, are administered to groups of test animals intravenously. The pulmonary arterial pressure (PAP), dynamic compliance (DC) of the lungs and lung lymph flow (LLF) are monitored continuously over a five-hour period.

Yet even still further even more, the compounds of formula I are useful in controlling hyperreactive airways induced by PAF or allergen, which property can be measured in accordance with the following procedure (Test G):

Male Hartley guinea pigs weighing 250 gm are sensitized to ovalbumin by aerosol inhalation exposure. The test animals are then subsequently rechallenged with ovalbumin aerosol repeatedly (3 to 6 times) over a period of two to three weeks. Airway reactivity is assessed by an acetylcholine dose response curve at times (1 to 3 days) after the last ovalbumin exposure. The test compound is assessed for its ability to control hyperreactivity airways by administering it orally with a gavage tube in an acceptable vehicle prior to each ovalbumin antigen exposure.

Yet even more still further even more, the compounds of formula I are useful in protecting against endotoxin-induced hypotension, which property can be measured according to the following procedure (Test H):

Male Sprague-Dawley rats weighing between 250 and 270 gm are anesthetized with sodium pentobarbital (50 mg/kg i.p.) and the left common carotid artery is cannulated (PE-50 tubing) and connected to a P50 pressure transducer. Mean arterial pressures and diastolic and systolic measurements are recorded using a Gould 2400S physiograph. Blood flow of the mesenteric artery is measured on a calibrated electromagnetic flowmeter probe. Blood is collected via the femoral artery into heparinized capillary tubes and centrifuged to determine hematocrit values.

Endotoxin from *E. coli* serotype 0111:B$_4$ is prepared fresh daily and administered by i.v. injection to the test animals in tris-Tyrode's buffer over a 1 to 50 mg/kg dosage range to establish a dose-response profile. The administration of endotoxin at 15 mg/kg i.v. produced a 54±8% decrease in mean arterial pressure and a corresponding 80% decrease in mesenteric artery blood flow. The test compound is assessed for its ability to protect against endotoxin-induced hypotension by administering it intravenously after endotoxin administration and measuring the recovery of blood pressure and mesenteric artery blood flow. The ED$_{50}$ value of the test compound is determined using linear regression fitting of inhibition profiles from 5 to 6 doses (3 animals per dose).

Lastly, the compounds of formula I are useful in protecting against endotoxin-induced death, which property can be measured according to the following procedure (Test I):

Healthy male BALB/c mice weighing between 24 and 27 g. are allowed to acclimate for 1 week with access to food and water. The test animals are then placed in a ventilated plexiglass restrainer that allows access to the tails. After the tails are allowed to immerse in warm water (38° C.) for 30 seconds, endotoxin from *E. coli* serotype 0111:B₄ is administered in a single injection at 2 ml/kg body weight to produce lethality at the desired effect of LD 70-90. The test compound is assessed for its ability to protect against endotoxin-induced death by administering it orally in a single bolus at a volume of 1 ml/kg body weight. Each treatment group consists of 7 to 10 test animals, every dosage is considered as a separate group and control groups are dosed with vehicles (water tris-Tyrodes's buffer, 1% CMC, etc) only. The percent mortality (or survival) is expressed by the number of deaths (or survivors) within the observation period. Values obtained are mean and standard error of mean of a single treatment which represents multiple days results for reproducibility. The $ED_{50}$ value of the test compound is determined using a Students t test (2 tail) for significance.

The compounds of formula I, and their pharmaceutically acceptable acid addition salts, may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositions may be prepared by conventional means.

The precise dosage of a compound of formula I, or a pharmaceutically acceptable acid addition salt thereof, to be employed for inhibiting platelet activating factor (PAF) depends upon several factors including the host, the nature and the severity of the condition being treated, the mode of administration and the particular compound employed. However, in general, satisfactory inhibition or antagonism of platelet activating factor is achieved when a compound of formula I, or a pharmaceutically acceptable acid addition salt thereof, is administered orally at a daily dosage of 0.05-100, preferably 0.1-30 mg/kg body weight or, for most larger primates, a daily dosage of 1-500 mg, preferably 1-50 mg. A typical oral dosage is 5 mg, three times a day.

As with the PAF inhibition use, the precise dosage of a compound of formula I, or a pharmaceutically acceptable acid addition salt thereof, to be employed in treating PAF-mediated bronchoconstriction and extravasation, PAF-induced hypotension, PAF-involved ischemic bowel disease, PAF-mediated, endotoxin-induced lung injury, for controlling hyperreactive airways induced by PAF or allergen and protecting against endotoxin-induced hypotension and death depends upon several factors including the host, the nature and severity of the condition being treated, the mode of administration and the particular compound employed. However, in general, satisfactory inhibition or antagonism of PAF-mediated bronchoconstriction and extravasation, PAF-induced hypotension, PAF-induced ischemic bowel disease, PAF-mediated, endotoxin-induced lung injury, control of hyperreactive airways induced by PAF or allergen and protection against endotoxin-induced hypotension and death is achieved when a compound of formula I, or a pharmaceutically acceptable acid addition salt thereof, is administered orally at a daily dosage of 0.2-100, preferably 0.2-50 mg/kg body weight or, for most larger primates, a daily dosage of 100-200 mg, preferably 10-350 mg. A typical oral dosage is 50 or 100 mg, two or three times a day.

Regardless of use, a small dosage is gradually increased until the optimal dosage for the host under treatment is determined. For administration by injection, a dosage somewhat lower than would be used for oral administration of the same compound to the same host having the same condition is usually employed.

The compounds of formula I, and their pharmaceutically acceptable acid addition salts, may be formulated into such pharmaceutical compositions containing an amount of the active substance that is effective for inhibiting PAF, in treating PAF-mediated bronchoconstriction and extravasation, in treating PAF-induced hypotension, in treating ischemic bowel disease, in treating PAF-mediated, endotoxin-induced lung injury, in controlling hyperreactive airways induced by PAF or allergen, and in protecting against endotoxin-induced hypotension and death, such compositions in unit dosage form and such compositions comprising a solid pharmaceutically acceptable carrier.

Tablets and capsules containing the ingredients indicated below may be prepared by conventional techniques and are useful as platelet activating factor inhibitors. The tablet may be administered once or twice a day whereas the capsule is suitably administered three times a day.

| Ingredients | Weight (mg) tablet | Weight (mg) capsule |
|---|---|---|
| compound of formula I, e.g., the compound of Example 1 | 5 | 5 |
| tragacanth | 10 | — |
| lactose (spray-dried) | 257.5 | 95 |
| corn starch | 15 | — |
| talcum | 10 | — |
| magnesium stearate | 2.5 | — |
| Total | 300.0 | 100 |

The following are representative of tablets and capsules which may be prepared by conventional means and are useful in treating PAF-mediated bronchoconstriction and extravasation, PAF-induced hypotension, PAF-involved ischemic bowel disease, PAF-mediated, endotoxin-induced lung injury, in controlling hyperreactive airways induced by PAF or allergen, and in protecting against endotoxin-induced hypotension and death. The tablet and the capsule may be suitably administered two or three times a day.

| Ingredients | Weight (mg) tablet | Weight (mg) capsule |
|---|---|---|
| compound of formula I, e.g., the compound of Example 1 | 50 | 50 |
| tragacanth | 10 | — |
| lactose (spray-dried) | 212.5 | 100 |
| corn starch | 15 | — |
| talcum | 10 | — |
| magnesium stearate | 2.5 | — |
| Total | 300.0 | 100 |

The following examples show representative compounds encompassed by this invention and their synthesis. However, it should be clearly understood that they are for purposes of illustration only.

EXAMPLE 1

1-methyl-6-[4-[2-(3,4,5-trimethoxyphenyl)ethyl]-phenyl]-4H-thieno[2,3-e][1,2,4]triazolo[3,4-c][1,4]diazepine

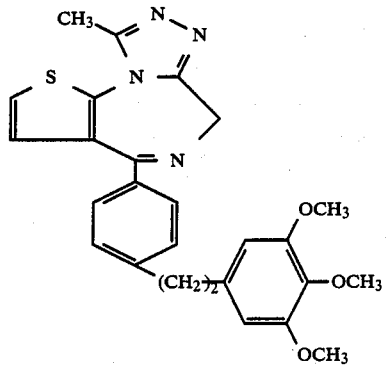

(a) Preparation of 3-oxo-3-[4-[2-(3,4,5-trimethoxyphenyl)ethyl]phenyl]-propanenitrile To a solution of 10 g (30 mmol) of methyl-4-[2-(3,4,5-trimethoxyphenyl)ethyl]benzoate and 1.74 ml (33 mmol) of acetonitrile in a mixture of 30 ml of dry N,N-dimethylformamide and 20 ml of dry tetrahydrofuran was added, portionwise under a nitrogen atmosphere at 0° C., 3 g (76 mmol) of a 60% suspension of sodium hydride in mineral oil. The resulting suspension was heated under a flow of nitrogen to 65° C. and maintained at this temperature for 2 hours. After cooling to 25° C., the resultant mixture was quenched with 3 ml of methanol and the solvent was removed in vacuo. The resultant residue was dissolved in 60 ml of water, acidified with 2N hydrochloric acid to a pH between 4 and 5 and then extracted with ethyl acetate. The combined organic phase was then washed successively with water and saturated sodium chloride solution and dried over magnesium sulfate, after which time the solvent was removed under reduced pressure. The crude product was then purified on silica gel employing a mixture of ethyl acetate and hexane in a 1:1 ratio as the eluent to yield a white crystalline solid.

(b) Preparation of 2-amino-3-thienyl-4-[2-(3,4,5-trimethoxyphenyl)ethyl]-phenylmethanone To a solution of 1.35 g of the compound prepared in (a) above in 8 ml of dry N,N-dimethylformamide was added, successively and under a nitrogen atmosphere, 0.6 g (4 mmol) of 1,4-dithiane-2,5-diol and 0.14 ml (1 mmol) of triethylamine, and the resultant mixture was heated to 50° C. and maintained at this temperature for 4 hours. After cooling the reaction mixture to 25° C., it was diluted with ethyl acetate and the resultant solution was washed successively with water and a saturated sodium chloride solution. The organic layer was dried over magnesium sulfate and evaporated under reduced pressure to yield a crude product which was purified on silica gel employing a mixture of ethyl acetate and hexane in a 1:1 ratio as the eluent to yield a yellow foam.

(c) Preparation of 2-bromo-N-3-[4-[2-(3,4,5-trimethoxyphenyl)ethyl]benzoyl]thienylacetamide To a solution of 1.3 g of the compound prepared in (b) above in 10 ml of dry methylene chloride was added, successively and under a nitrogen atmosphere, 0.74 ml (4.2 mmol) of N,N-diisopropylethylamine and 0.31 ml (3.6 mmol) of bromoacetylbromide, and the resultant mixture was stirred at ambient temperature for 3 days. The reaction mixture was diluted with methylene chloride, washed successively with water and a saturated sodium chloride solution, and dried over magnesium sulfate. The solvent was then removed under reduced pressure to yield a crude product which was purified by column chromatography on silica gel employing a mixture of ethyl acetate and hexane in a 1:1 ratio at the eluent to yield a yellow foam.

(d) Preparation of 2-amino-N-3-[4-[2-(3,4,5-trimethoxyphenyl)ethyl]benzoyl]thienylacetamide Dry ammonia gas was bubbled into a solution of 1 g of the compound prepared in (c) above in a mixture of 10 ml of dry methanol and 10 ml of dry tetrahydrofuran for 5 minutes, and the resultant mixture was stirred at ambient temperature for 16 hours in a closed system. The solvent was evaporated in vacuo and the crude residue was purified by column chromatography on silica gel employing a mixture of ethyl acetate and hexane in increasing amounts of the latter, the initial ratio being 1:1 by volume, with elution taking place when the ratio became 1:5 by volume and resulted in a yellow foam.

(e) Preparation of 1,3-dihydro-5-[4-[2-(3,4,5-trimethoxyphenyl)ethyl]-phenyl]-2H-thieno[2,3-e][1,4]diazepin-2-one To a solution of 0.66 g (1.45 mmol) of the compound prepared in (d) above in 15 ml of dry toluene was added 1.5 g of silica gel (70–230 mesh), and the resultant mixture was heated to reflux and maintained at reflux temperature for 2 hours using a Dean-Stark trap. After cooling the reaction mixture to 25° C., it was filtered and the silica gel was washed with hot methanol. The combined organic phase was then evaporated to yield a yellow foam.

(f) Preparation of 1,3-dihydro-5-[4-[2-(3,4,5-trimethoxyphenyl)ethyl]-phenyl]-2H-thieno[2,3-e][1,4]diazepin-2-thione To a solution of 0.6 g (1.4 mmol) of the compound prepared in (e) above in 30 ml of dry pyridine was added 0.37 g (0.82 mmol) of phosphorus pentasulfide, and the resultant mixture was heated to 90° C. and maintained at this temperature for 30 minutes under a nitrogen atmosphere. After cooling the reaction mixture to 25° C., the solvent was evaporated and the resultant residue was diluted with methylene chloride. The organic phase was then washed successively with water and brine, dried over anhydrous magnesium sulfate and evaporated to yield a red foam.

PREPARATION OF THE TITLE COMPOUND

To a solution of 0.52 g (1.1 mmol) of the compound prepared in (f) above in 15 ml of dry diglyme was added 0.426 g (5.7 mmol) of acethydrazide, and the resultant mixture was heated to 110° C. under a nitrogen atmosphere and maintained at this temperature for 4 hours. After cooling the reaction mixture to 25° C., the solvent was evaporated in vacuo and the resultant residue was diluted with methylene chloride, washed successively with water and brine, and dried over anhydrous magnesium sulfate. The solvent was then evaporated under reduced pressure to yield a crude product which was purified by column chromatography on silica gel employing a mixture of methylene chloride and methanol in a 20:1 ratio as the eluent to yield the title compound as a yellow solid, m.p. 264° C.

| PAIA test | IC$_{50}$ | 12.0 uM |
| Test A | IC$_{50}$ | 0.22 uM |
| Test B | ED$_{50}$ | 0.8 mg/kg p.o. |
| Test C | ED$_{50}$ | 0.5 mg/kg p.o. |

EXAMPLE 2

9-Methyl-4-[4-[2-(3,4,5-trimethoxyphenyl)ethyl]-phenyl]-6H-thieno[3,2-f][1,2,4]triazolo[4,3-a][1,4]diazepine-2-propanoic acid, methyl ester or (8-methoxycarbonylethyl-1-methyl-6-[4-[2-(3,4,5-trimethoxyphenyl)ethyl]phenyl]-4H-thieno[2,3-e][1,2,4]triazolo[3,4-c][1,4]diazepine)

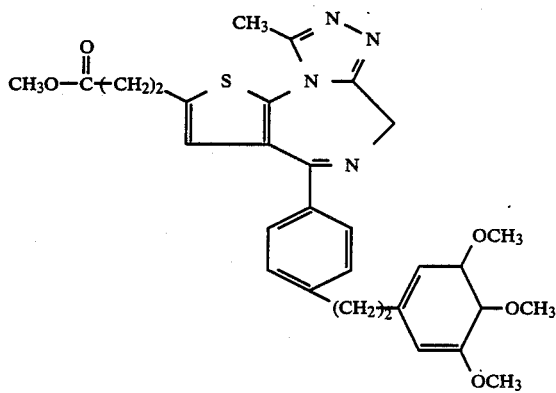

(a) Preparation of 1-oxopentanoic acid, methyl ester

To a solution of 8.23 g (50 mmol) of methyl 4-(chloroformyl)butyrate in 200 ml of tetrahydrofuran were added 5.4 g (50 mmol) of 2,6-lutidine and 0.75 g of 10% palladium on carbon, and the resultant mixture was then hydrogenated under a 41 p.s.i. atmosphere of hydrogen gas (Parr Shaker) for 3 hours. The reaction mixture was then filtered and the filtrate was evaporated under reduced pressure to obtain an oil which was washed with diethyl ether and then filtered. The resultant filtrate was then evaporated to yield a clear liquid.

(b) Preparation of 5-amino-4-[4-[2-(3,4,5-trimethoxyphenyl)ethyl]benzoyl]-2-thiophene propanoic acid, methyl ester A mixture of 1.53 g (12 mmol) of the compound prepared in (a) above, 4 g (12 mmol) of the compound prepared in (a) of Example 1 and 0.42 g of sulfur in 10 ml of N,N-dimethylformamide was heated to 70° C. and maintained at this temperature for 1 hour, after which time 1 ml of triethylamine was added to the mixture. The resultant mixture was stirred at 70° C. for an additional 30 minutes, and then the reaction mixture was cooled to ambient temperature. The solvent was then evaporated and the resultant residue was diluted with ethyl acetate. The resultant solution was then washed successively with water and brine, dried over magnesium sulfate and filtered. The solvent was then removed under reduced pressure and the crude product was purified by column chromatography on silica gel employing a mixture of ethyl acetate and hexane in a 1:1 ratio as the eluent to yield a brown gum.

(c) Preparation of 5-[2-[1-oxo-2-(phenylmethoxycarbonylamino)ethyl]amino]-4-[4-[2-(3,4,5-trimethoxyphenyl)ethyl]benzoyl]-2-thiophenepropanoic acid, methyl ester To a suspension of 2.24 g (11 mmol) of carbobenzyloxyglycine in 60 ml of dry ether was added, under a nitrogen atmosphere, 1.75 g (8.4 mmol) of phosphorus pentachloride, and the resultant mixture was stirred for 1 hour at room temperature. The resultant solution was then added to a solution of 3.7 g (7.7 mmol) of the compound prepared in (b) above in 30 ml of chloroform via cannular. The reaction mixture was then stirred for 16 hours at room temperature, diluted with methylene chloride, and the resultant solution was washed successively with water, a saturated sodium bicarbonate solution and brine. The organic layer was then dried over magnesium sulfate, filtered and the solvent was removed under reduced pressure. The crude product was then purified by column chromatography on silica gel employing a mixture of ethyl acetate and hexane in decreasing amounts of the latter, the initial ratio being 1:2 by volume, with elution taking place when the ratio became 1:1 by volume and resulted in a yellow foam.

(d) Preparation of 5-[(2-amino-1-oxoethyl)amino]-4-[4-[2-(3,4,5-trimethoxyphenyl)ethyl]benzoyl]-2-thiophenepropanoic acid, methyl ester To a solution of 2.2 g (3.3 mmol) of the compound prepared in (c) above in 100 ml of glacial acetic acid was added 2.2 g of 10% palladium on carbon, and the resultant mixture was then stirred under a hydrogen atmosphere for 16 hours. The reaction mixture was then filtered and the filtrate was evaporated under reduced pressure to obtain an oil which was dissolved in ethyl acetate. The resultant solution was then washed successively with water, a saturated sodium bicarbonate solution and brine. The organic layer was then dried over magnesium sulfate, filtered and the solvent was removed under reduced pressure to yield the desired product.

(e) Preparation of 7,8-dihydro-7-oxo-4-[4-[2-(3,4,5-trimethoxyphenyl)ethyl]phenyl]-6H-thieno[2,3-e][1,4]-diazepine-2-propanoic acid, methyl ester Following essentially the procedure of Example (1e), and using in place of the compound prepared in Example (1d), an approximately equivalent amount of the compound prepared in (d) above, a yellow foam was obtained.

(f) Preparation of 7,8-dihydro-7-thioxo-4-[4-[2-(3,4,5-trimethoxyphenyl)ethyl]phenyl]-6H-thieno[2,3-e][1,4]-diazepine-2-propanoic acid, methyl ester Following essentially the procedure of Example (1f), and using in place of the compound prepared in Example (1e), an approximately equivalent amount of the compound prepared in (e) above, a reddish orange foam was obtained.

PREPARATION OF THE TITLE COMPOUND

Following essentially the last step of the procedure for preparing the compound of Example 1, and using in place of the compound prepared in Example (1f), an approximately equivalent amount of the compound prepared in (f) above, the title compound was obtained as a yellow solid, m.p. 78°–80° C.

EXAMPLE 3

3-[9-Methyl-4-[4-[2-(3,4,5-trimethoxyphenyl)ethyl]-phenyl]-6H-thieno[3,2-f][1,2,4]triazolo[4,3-a][1,4]diazepin-2-yl]-1-oxopropylmorpholine or (1-methyl-8-morpholinocarbonylethyl-6-[4-[2-(3,4,5-trimethoxyphenyl)ethyl]phenyl]-4H-thieno[2,3-e][1,2,4]triazolo[3,4-c][1,4]diazepine)

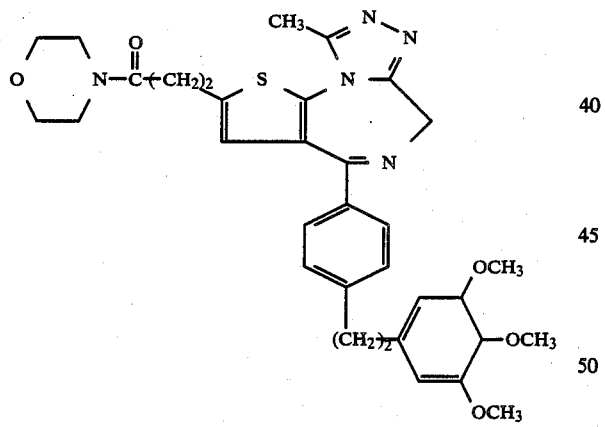

A solution of 0.33 g (0.59 mmol) of the compound of Example 2 in 3 ml of dry morpholine was heated at 180° C. in a sealed tube for 5 hours, and then cooled to room temperature. The solvent was evaporated and the resultant residue was purified by column chromatography on silica gel employing a mixture of methylene chloride and methanol in a 9:1 ratio as the eluent to yield the title compound as a tan solid, m.p. 105°–107° C.

EXAMPLE 4

9-Methyl-4-[4-[2-(3,4,5-trimethoxyphenyl)ethyl]-phenyl]-6H-thieno[3,2-f][1,2,4]triazolo[4,3-a][1,4]diazepine-2-propanoic acid, sodium salt of (8-carboxyethyl-1-methyl-6-[4-[2-(3,4,5-trimethoxyphenyl)ethyl]phenyl]-4H-thieno[2,3-e][1,2,4]triazolo[3,4-c][1,4]diazepine, sodium salt)

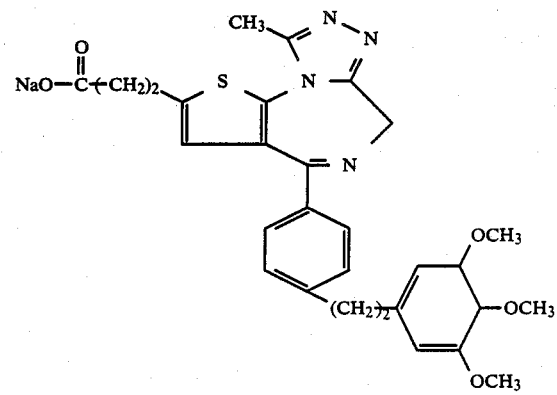

To a solution of 0.06 g (0.11 mmol) of the compound of Example 2 in 1 ml of ethanol was added, with stirring, a 1N solution of sodium hydroxide which was pre-cooled to 0° C. The resultant solution was then stirred for 30 minutes while the temperature was maintained at 0° C. Diethyl ether was then added and the resulting precipitate was filtered and dried to yield the title compound as a tan solid, m.p. 190° C.

EXAMPLE 5

6-[2-Chloro-4-[2-(3,4,5-trimethoxyphenyl)ethyl]-phenyl]-1-methyl-4H-thieno[2,3-e][1,2,4]triazolo[3,4-c][1,4]-diazepine

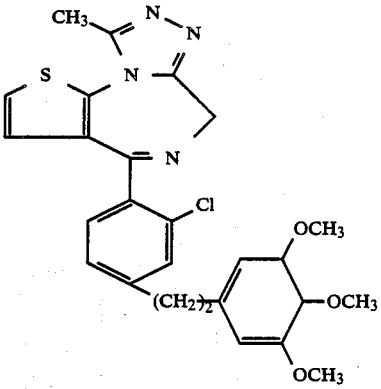

(a) Preparation of 2-chloro-β-oxo-4-[2-[3,4,5-trimethoxyphenyl)ethyl]benzenepropanenitrile Following essentially the procedure of Example (1a), and using in place of methyl-4-[2-(3,4,5-trimethoxyphenyl)ethyl]benzoate, an approximately equivalent amount of 2-chloro-4-[2-(3,4,5-trimethoxyphenyl)ethyl]benzoic acid, methyl ester, a white solid was obtained.

(b) Preparation of 2-amino-3-thienyl-2-chloro-4-[2-(3,4,5-trimethoxyphenyl)ethyl]methanone Following essentially the procedure of Example (1b), and using in place of the compound prepared in Example (1a), an approximately equivalent amount of the compound prepared in (a) above, a yellow oil was obtained.

(c) Preparation of bromo-N-[3-[2-chloro-4-[2-(3,4,5-trimethoxyphenyl)ethyl]benzoyl]thien-2-yl]acetamide To a solution of 0.57 g of the compound prepared in (b) above in 5 ml of toluene was added, successively at ice water bath temperature, 0.64 ml of pyridine and 0.34 ml (3.9 mmol) of bromoacetylbromide, and the resultant mixture was stirred at room temperature for 16 hours. The reaction mixture was diluted with ethyl acetate, washed successively with water and brine, and dried over magnesium sulfate. The solvent was evaporated to yield a brown oil.

(d) Preparation of amino-N-[3-[2-chloro-4-[2-(3,4,5-trimethoxyphenyl)ethyl]benzoyl]thien-2-yl]acetamine Following essentially the procedure of Example (1d), and using in place of the compound prepared in Example (1c), an approximately equivalent amount of the compound prepared in (c) above, a yellow foam was obtained.

(e) Preparation of 1,3-dihydro-5-[2-chloro-4-[2-(3,4,5-trimethoxyphenyl)ethyl]phenyl]-2H-thieno-[2,3-e][1,4]diazepin-2-one Following essentially the procedure of Example (1e), and using in place of the compound prepared in Example (1d), an approximately equivalent amount of the compound prepared in (d) above, a yellow foam was obtained.

(f) Preparation of 1,3-dihydro-5-[2-chloro-4-[2-(3,4,5-trimethoxyphenyl)ethyl]phenyl]-2H-thieno-[2,3-e][1,4]diazepin-2-thione To a solution of 0.25 g (0.53 mmol) of the compound prepared in (e) above in 5 ml of toluene was added 0.13 g (0.32 mmol) of Lawesson's Reagent, and the resultant mixture was heated to 90° C. and maintained at this temperature for 3 hours. After cooling the reaction mixture to 25° C., the solvent it was diluted with 50 ml methylene chloride, washed successively with 1 ml of water and 10 ml of brine, dried over magnesium sulfate and evaporated. The crude residue was pruified by column chromatography on silica gel employing a mixture of ethyl acetate and hexane in 2:1 ratio as the eluent to yield an orange foam.

PREPARATION OF THE TITLE COMPOUND

Following essentially the last step of the procedure for preparing the compound of Example 1, and using in place of the compound of Example (1f), an approximately equivalent amount of the comound prepared in (f) above, the title compound was obtained as a light brown solid, m.p. 178°–180° C.

What is claimed is:

1. A compound of formula I:

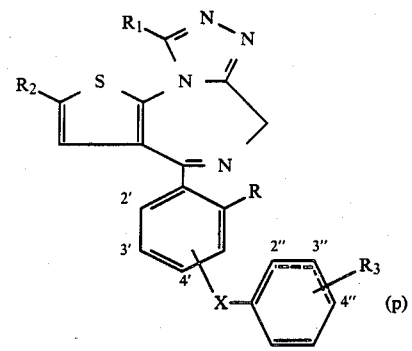

where
$R$ is hydrogen or chloro;
$R_1$ is hydrogen; methyl or cyclopropyl;
$R_2$ is hydrogen; methyl; ethyl; a group of the formula

where m is 1 to 4 and $R_4$ is methyl, ethyl or an alkali metal cation; a group of the formula

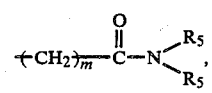

where m is as defined above and each $R_5$, independently, is straight or branched chain $C_{1-3}$ alkyl, or the two $R_5$'s together with the nitrogen atom to which they are attached form a group of the formula

where n is 4 or 5, or a group of the formula

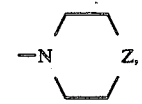

where Z is —O—, —S— or —NCH$_3$—; or a group of the formula

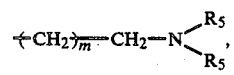

where m and the $R_5$'s are as defined above;
X is CH$_{2m}$ where m is as defined above; —OCH$_2$— or —CH$_2$OCH$_2$—;
P is 0 or an integer 1 to 3; and
$R_3$ is chloro; fluoro; methyl; t-butyl; OR$_6$, where R$_6$ is methyl or ethyl; or a group

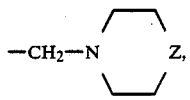

where Z is as defined above; with the provisos that: (1) when R is hydrogen, X is only in the 3'- or 4'-positions, and when R is chloro, X is only in the 4'-position; (2) when $R_3$ is chloro, fluoro or methyl, the maximum number of said substituents is two; (3) when $R_3$ is t-butyl or a group

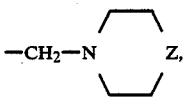

then p is 1; and (4) when p is 2, the $R_3$'s cannot be in the 2''- and 6''-positions, simultaneously; or a pharmaceutically acceptable acid addition salt thereof.

2. A compound according to claim 1 of formula I':

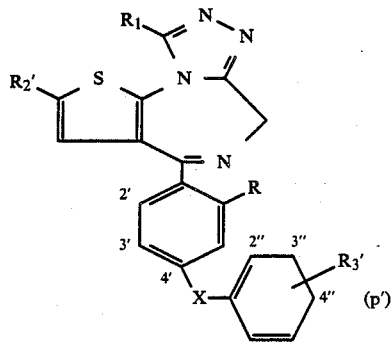

where
$R_2'$ is hydrogen; a group of the formula

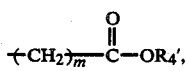

where $R_4'$ is methyl, ethyl, sodium or potassium and m is as defined in claim 1; or a group of the formula

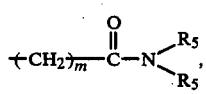

where m and the $R_5$'s are as defined in claim 1; p' is an integer 1 to 3;
$R_3'$ is $OR_6$, where $R_6$ is as defined in claim 1; or a group

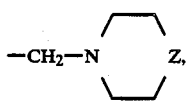

where Z is as defined in claim 1; and

R, $R_1$ and X are as defined in claim 1; with the provisos that: (1) when $R_3'$ is a group

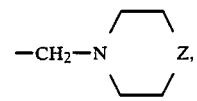

then p' is 1; and (2) when p' is 2, the $R_3'$'s cannot be in the 2''- and 6''-positions, simultaneously; or a pharmaceutically acceptable acid addition salt thereof.

3. A compound according to claim 2 of formula I'':

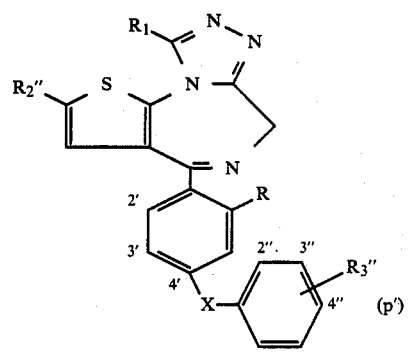

where
$R_2''$ is hydrogen; a group of the formula

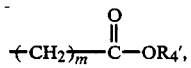

where m and $R_4'$ are as defined in claim 2; or a group of the formula

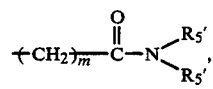

where m is as defined above and the $R_5$'s together with the nitrogen atom to which they are attached form a group of the formula

where n is 4 or 5 or a group of the formula

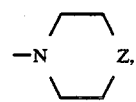

where Z is as defined in claim 2;
$R_3''$ is $OR_6$, where $R_6$ is as defined in claim 2; and
R, $R_1$, X and p' are as defined in claim 2, with the proviso that when p' is 2, the $R_3'''$'s cannot be in the 2''- and 6''-positions, simultaneously; or a pharmaceutically acceptable acid addition salt thereof.

4. A compound according to claim 3 of formula I''':

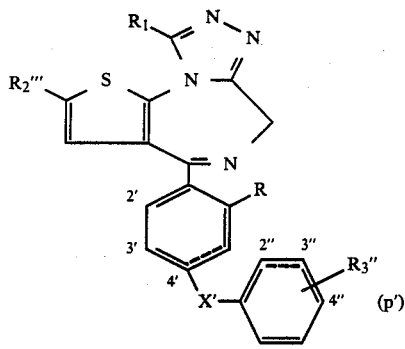

where
R$_2'''$ is hydrogen; a group of the formula

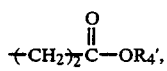

where R$_4'$ is as defined in claim 3; or a group of the formula

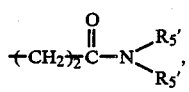

where the R$_5'$'s are as defined in claim 3;
X' is $-(CH_2)_m-$, where m is as defined in claim 3; and
R, R$_1$, p' and R$_3''$ are as defined in claim 3; with the proviso that when p' is 2, the R$_3'''$s cannot be in the 2''- and 6''-positions, simulatneously;
or a pharmaceutically acceptable acid addition salt thereof.

5. A compound according to claim 4 of formula I$^{IV}$;

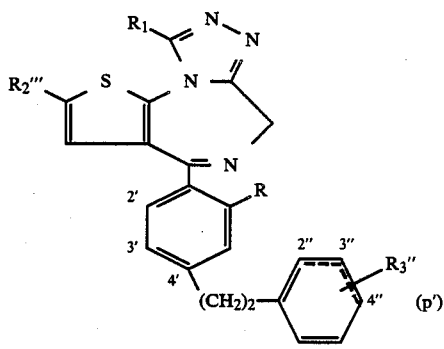

where R, R$_1$, R$_2'''$, p' and R$_3''$ are as defined in claim 4, with the proviso that when p' is 2, the R$_3'''$s cannot be in the 2''- and 6''-positions, simultaneously;
or a pharmaceutically acceptable acid addition salt thereof.

6. A compound according to claim 5 having the formula

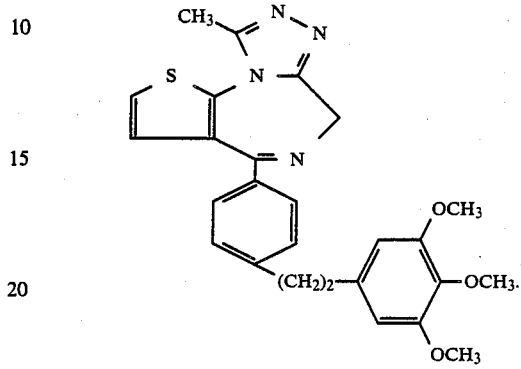

7. A compound according to claim 5 having the formula

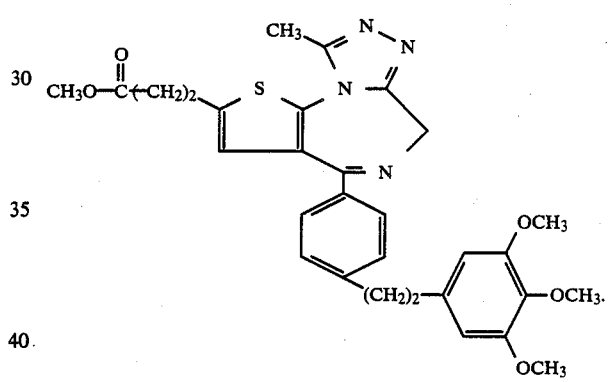

8. A compound according to claim 5 having the formula

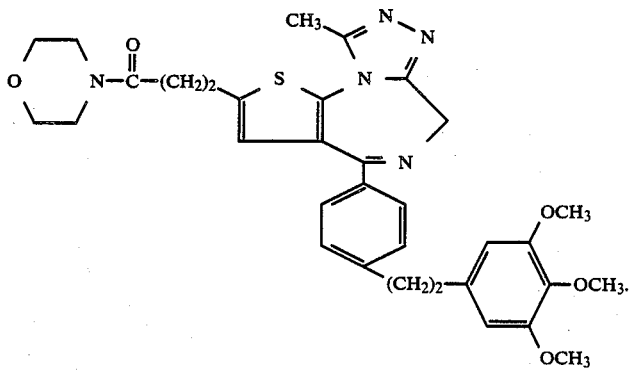

9. A compound according to claim 5 having the formula

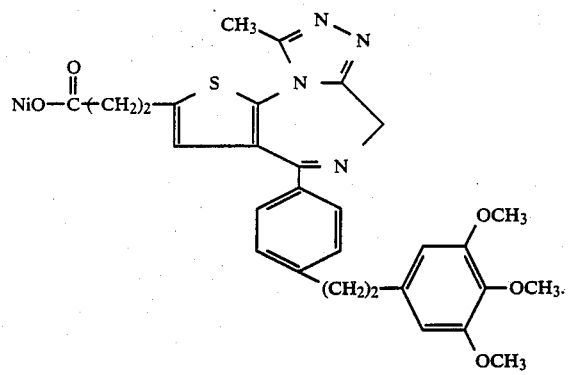

10. A compound according to claim 5 having the formula

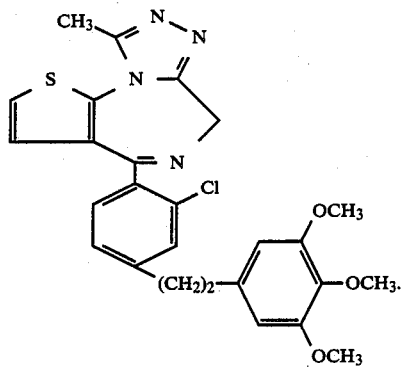

11. A method of inhibiting PAF-induced blood platelet aggregation comprising administering to a subject afflicted therewith a therapeutically effective amount of a compound according to claim 1, or a pharmaceutically acceptable acid addition salt thereof.

12. A method according to claim 11 comprising administering a therapeutically effective amount of the compound of the formula

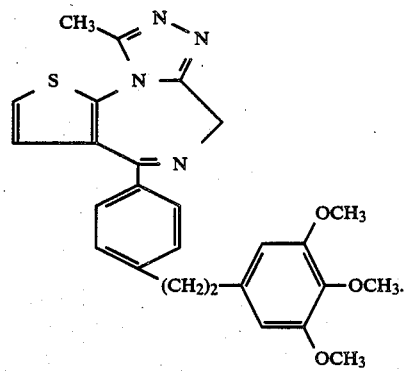

13. A method of inhibiting PAF-mediated bronchoconstriction and extravasation comprising administering to a subject afflicted therewith a therapeutically effective amount of a compound according to claim 1, or a pharmaceutically acceptable acid addition salt thereof.

14. A method according to claim 13 comprising administering a therapeutically effective amount of the compound of the formula

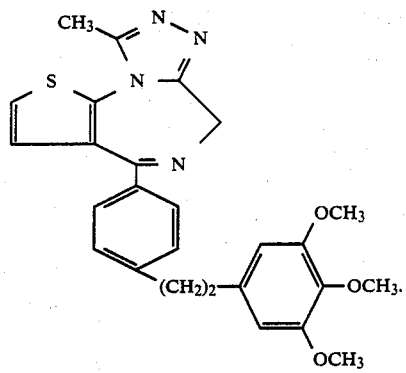

15. A method of inhibiting PAF-induced hypotension comprising administering to a subject afflicted therewith a therapeutically effective amount of a compound according to claim 1, or a pharmaceutically acceptable acid addition salt thereof.

16. A method of inhibiting PAF-induced ischemic bowel disease comprising administering to a subject afflicted therewith a therapeutically effective amount of a compound according to claim 1, or a pharmaceutically acceptable acid addition salt thereof.

17. A method of inhibiting PAF-mediated, endotoxin-induced lung injury comprising administering to a subject afflicted therewith a therapeutically effective amount of a compound according to claim 1, or a pharmaceutically acceptable acid addition salt thereof.

18. A method of inhibiting PAF-mediated, endotoxin-induced septic shock comprising administering to a subject afflicted therewith a therapeutically effective amount of a compound according to claim 1, or a pharmaceutically acceptable acid addition salt thereof.

19. A method of inhibiting PAF-mediated, endotoxin-induced adult respiratory distress syndrome comprising administering to a subject afflicted therewith a therapeutically effective amount of a compound according to claim 1, or a pharmaceutically acceptable acid addition salt thereof.

20. A method of controlling hyperreactive airways induced by PAF or allergen comprising administering to a subject afflicted therewith a therapeutically effective amount of a compound according to claim 1, or a pharmaceutically acceptable acid addition salt thereof.

21. A method of protecting against endotoxin-induced hypotension comprising administering to a subject afflicted therewith a therapeutically effective amount of a compound according to claim 1, or a pharmaceutically acceptable acid addition salt thereof.

22. A method of protecting against endotoxin-induced death comprising administering to a subject afflicted therewith a therapeutically effective amount of a compound according to claim 1, or a pharmaceutically acceptable acid addition salt thereof.

23. A pharmaceutical composition useful in inhibiting PAF-induced blood platelet aggregation, PAF-mediated bronchoconstriction and extravasation, PAF-induced hypotension, PAF-induced ischemic bowel disease and PAF-mediated endotoxin-induced lung injury, for controlling hyperreactive airways and for protecting against endotoxin-induced hypotension and death comprising a pharmaceutically acceptable carrier and a therapeutically effective amount of a compound according to claim 1, or a pharmaceutically acceptable acid addition salt thereof.

* * * * *